く1>

United States Patent
Morikawa et al.

(10) Patent No.: US 10,586,880 B2
(45) Date of Patent: Mar. 10, 2020

(54) SOLAR CELL MANUFACTURING METHOD

(71) Applicant: Mitsubishi Electric Corporation, Chiyoda-ku, Tokyo (JP)

(72) Inventors: Hiroaki Morikawa, Tokyo (JP); Hirohisa Nishino, Tokyo (JP); Yukiko Nakazawa, Tokyo (JP); Atsuro Hama, Tokyo (JP); Yuichiro Hosokawa, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 15/743,099

(22) PCT Filed: Oct. 21, 2015

(86) PCT No.: PCT/JP2015/079744
§ 371 (c)(1),
(2) Date: Jan. 9, 2018

(87) PCT Pub. No.: WO2017/068671
PCT Pub. Date: Apr. 27, 2017

(65) Prior Publication Data
US 2019/0081188 A1    Mar. 14, 2019

(51) Int. Cl.
*H01L 27/30* (2006.01)
*H01L 31/0216* (2014.01)
(Continued)

(52) U.S. Cl.
CPC ... *H01L 31/02168* (2013.01); *G01N 21/8806* (2013.01); *H01L 22/10* (2013.01);
(Continued)

(58) Field of Classification Search
CPC ............ H01L 31/0687; H01L 31/0725; H01L 31/076; H01L 31/078
See application file for complete search history.

(56) References Cited

U.S. PATENT DOCUMENTS 6,236,044 B1  5/2001  Chou et al.
8,048,814 B2  11/2011  Meisel et al.
(Continued)

FOREIGN PATENT DOCUMENTS

CN    201824657 U    5/2011
CN    102318078 A    1/2012
(Continued)

OTHER PUBLICATIONS

Office Action (Notification of Reasons for Refusal) dated Jul. 10, 2018 , by the Japanese Patent Office in corresponding Japanese Patent Application No. 2017-546330 and English translation of the Office Action. (6 pages).

(Continued)

*Primary Examiner* — Mohammad M Choudhry
(74) *Attorney, Agent, or Firm* — Buchanan Ingersoll & Rooney PC (57) ABSTRACT

A solar cell manufacturing method includes a step of forming a diffusion layer including a first section and a second section on a light-receiving side of a semiconductor substrate, where the first section has a first concentration of impurities, and the second section has a second concentration of the impurities that is higher than the first concentration, a step of irradiating the diffusion layer with detection light that is reflected at a higher reflectivity on the first section than on the second section, and a step of detecting the first section that corresponds to a first reflectivity, and the second section that corresponds to a second reflectivity that is lower than the first reflectivity in the diffusion layer on the (Continued)

basis of a difference in reflectivity of the detection light reflected off the respective sections of the diffusion layer.

5 Claims, 6 Drawing Sheets

(51) Int. Cl.
*H01L 21/66* (2006.01)
*H01L 31/18* (2006.01)
*G01N 21/88* (2006.01)
*H01L 31/0224* (2006.01)
*H01L 31/068* (2012.01)

(52) U.S. Cl.
CPC .... *H01L 31/022425* (2013.01); *H01L 31/068* (2013.01); *H01L 31/1804* (2013.01); *H01L 31/1876* (2013.01); *Y02E 10/50* (2013.01); *Y02P 70/521* (2015.11)

(56) References Cited

U.S. PATENT DOCUMENTS

| | | |
|---|---|---|
| 8,288,176 B2 | 10/2012 | Meisel et al. |
| 8,697,987 B2 | 4/2014 | Cotal et al. |
| 2001/0054693 A1 | 12/2001 | Chou et al. |
| 2012/0040490 A1 | 2/2012 | Gallazzo et al. |
| 2014/0069498 A1 | 3/2014 | Cho et al. |

FOREIGN PATENT DOCUMENTS

| | | |
|---|---|---|
| CN | 103674974 A | 3/2014 |
| JP | 2000-65759 A | 3/2000 |
| JP | 2012-514851 A | 6/2012 |
| JP | 2012-527777 A | 11/2012 |
| JP | 2013-232607 | 11/2013 |
| JP | 2014-7188 A | 1/2014 |
| TW | 201248893 A | 12/2012 |

OTHER PUBLICATIONS

International Search Report (PCT/ISA/210) dated Dec. 15, 2015, by the Japanese Patent Office as the International Searching Authority for International Application No. PCT/JP2015/079744.

Written Opinion (PCT/ISA/237) dated Dec. 15, 2015, by the Japanese Patent Office as the International Searching Authority for International Application No. PCT/JP2015/079744.

Economic Department Department of Intellectual Property examination opinion letter of advice dated Mar. 30, 2017 (Taiwan Application No. 105109991), with computer generated English translation.

Office Action (First Notification of Reasons for Refusal) dated Mar. 4, 2019, by the State Intellectual Property Office of People's Republic of China in corresponding Chinese Patent Application No. 201580082173.5 and a partial translation of the Office Action. (11 pages).

Office Action dated Sep. 26, 2019, by the Chinese Patent Office in corresponding Chinese Patent Application No. 201580082173.5 and partial English translation of the Office Action. (12 pages).

| WAVELENGTH OF DETECTION LIGHT (nm) | DIFFERENCE IN REFLECTIVITY (POINT) | | |
|---|---|---|---|
| | LOWER LIMIT THICKNESS | STANDARD THICKNESS | UPPER LIMIT THICKNESS |
| 392 | 2.87 | 3.82 | 1.08 |
| 396 | 2.55 | 4.16 | 1.55 |
| 402 | 2.28 | 4.05 | 2.04 |
| 408 | 2.03 | 4.13 | 2.47 |
| 417 | 1.60 | 3.87 | 2.97 |
| 434 | 1.08 | 3.23 | 3.25 |

SOLAR CELL MANUFACTURING METHOD

FIELD

The present invention relates to a solar cell manufacturing method that converts optical energy to power with high efficiency.

BACKGROUND

Solar cells have been developed in which the concentration of impurities is relatively high and the electrical resistance is relatively low below an electrode arranged on a light-receiving side, and the concentration of impurities is relatively low and the electrical resistance is relatively high below a section that receives light other than the section where the electrode is arranged. In the above solar cell, the electrical resistance that affects energy conversion is low, and recombination of electrons with positive holes on the light-receiving side is comparatively suppressed. Therefore, the solar cell can convert optical energy to power with high efficiency.

The solar cell has a selective emitter structure. Conventionally, a method using screen printing has been commonly known as a method to form a light-receiving-side electrode in the solar cell with a selective emitter structure. More specifically, as a method to detect a position of a light-receiving-side electrode to be formed by screen printing, it is common to use three points on an outer periphery of a semiconductor substrate as reference points to indirectly detect a position where a light-receiving-side electrode should be formed.

As a method to detect a position, there has been proposed a method in which a semiconductor substrate, formed with a high-concentration selective diffusion layer, is irradiated with light that passes through the semiconductor substrate to detect a position where a light-receiving-side electrode should be formed on the basis of an intensity distribution of the light having passed through the semiconductor substrate (see, for example, Patent Literature 1). There has also been proposed a method in which silicon nanoparticles are deposited on the surface of a semiconductor substrate, and the region of the silicon nanoparticles is irradiated with light to detect a position by using the reflectivity of the light (see, for example, Patent Literature 2).

CITATION LIST

Patent Literatures

Patent Literature 1: Japanese Patent Application Laid-open No. 2013-232607
Patent Literature 2: Japanese Patent Application National Publication No. 2012-527777

SUMMARY

Technical Problem

However, in the above method that uses three points on an outer periphery of a semiconductor substrate as reference points to detect the position where a light-receiving-side electrode should be formed, the installation position of the semiconductor substrate may become slightly misaligned. Therefore, it is very difficult to accurately detect the position where the light-receiving-side electrode should be formed. This results in a problem that the light-receiving-side electrode may be formed at a position misaligned from an intended position. In the method described in Patent Literature 1, because transmissive light is used, it is necessary to provide an irradiation unit beside one surface of the semiconductor substrate, and also provide a detection unit beside the other surface. This results in a problem that the device configuration for implementing this method becomes more complicated. The method described in Patent Literature 2 has a problem that special materials that are silicon nanoparticles are required.

The present invention has been made in view of the above, and an object of the present invention is to provide a solar cell manufacturing method for accurately detecting a position where a light-receiving-side electrode should be formed, and forming the light-receiving-side electrode at a detected position without a device having a complicated configuration and without requiring special materials.

Solution to Problem

To solve the above-described problem and attain the object, the present invention includes: a step of forming a diffusion layer including a first section and a second section on a light-receiving side of a semiconductor substrate, where the first section has a first concentration of impurities and has a first resistance value, and the second section has a second concentration of the impurities that is higher than the first concentration and has a second resistance value that is smaller than the first resistance value; a step of irradiating the diffusion layer with detection light that is reflected at a higher reflectivity on the first section than on the second section, and that has a wavelength between 392 nm and 470 nm; a step of detecting the first section that corresponds to a first reflectivity, and the second section that corresponds to a second reflectivity that is lower than the first reflectivity in the diffusion layer on a basis of a difference in reflectivity of the detection light reflected off respective sections of the diffusion layer; and a step of forming a light-receiving-side electrode on the detected second section.

Advantageous Effects of Invention

According to the present invention, an effect is obtained where it is possible to obtain a solar cell manufacturing method for accurately detecting a position where a light-receiving-side electrode should be formed, and forming the light-receiving-side electrode at a detected position without a device having a complicated configuration and without requiring special materials.

DESCRIPTION OF EMBODIMENT

A solar cell manufacturing method according to embodiment of the present invention will be described in detail below with reference to the accompanying drawings. The present invention is not limited to the embodiment.

First Embodiment

Figure 1:
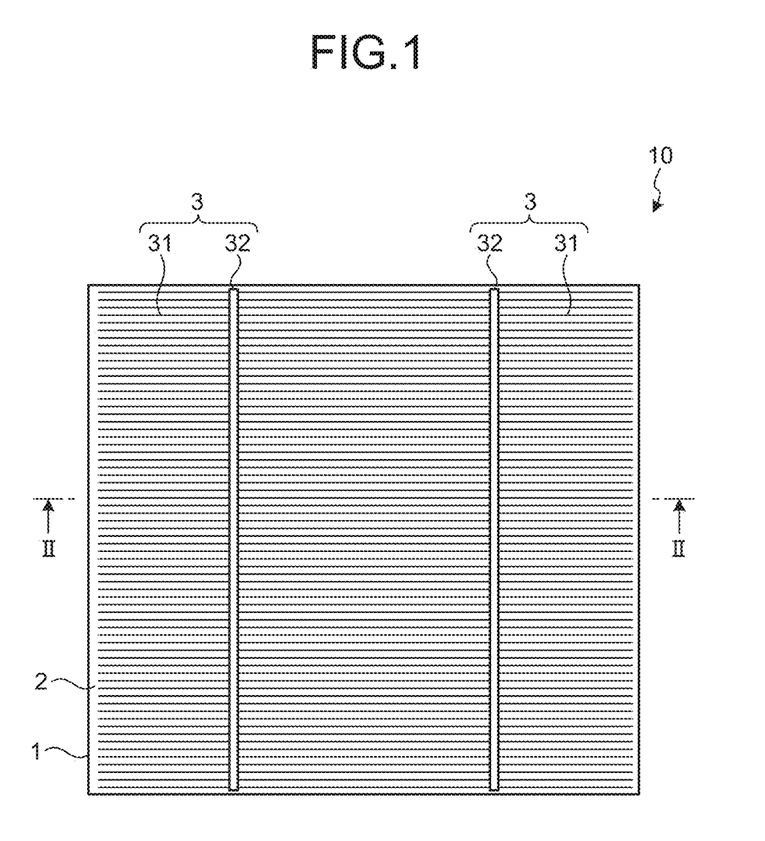
FIG. 1 is a diagram illustrating a light-receiving side of a solar cell manufactured by a solar cell manufacturing method according to a first embodiment.

Prior to explaining a solar cell manufacturing method according to a first embodiment, a solar cell manufactured by the solar cell manufacturing method is described below. FIG. 1 is a diagram illustrating a light-receiving side of a solar cell 10 manufactured by the solar cell manufacturing method according to the first embodiment. The solar cell 10 is a selective-emitter type crystalline silicon-based solar cell.

As illustrated in FIG. 1, the solar cell 10 includes a semiconductor substrate 1, an anti-reflective film 2, and a light-receiving-side electrode 3. The anti-reflective film 2 is provided on a light-receiving side of the semiconductor substrate 1. The light-receiving-side electrode 3 is also provided on the light-receiving side of the semiconductor substrate 1. The light-receiving-side electrode 3 includes a plurality of grid electrodes 31 that collect electricity generated in the semiconductor substrate 1, and a plurality of bus electrodes 32 through which electricity collected by the grid electrodes 31 is extracted to the outside of the solar cell 10. Each of the grid electrodes 31 is a linear electrode, and is parallel to one another. Each of the bus electrodes 32 is also a linear electrode, and is parallel to one another. The bus electrodes 32 and the grid electrodes 31 cross each other at right angles.

Figure 2:
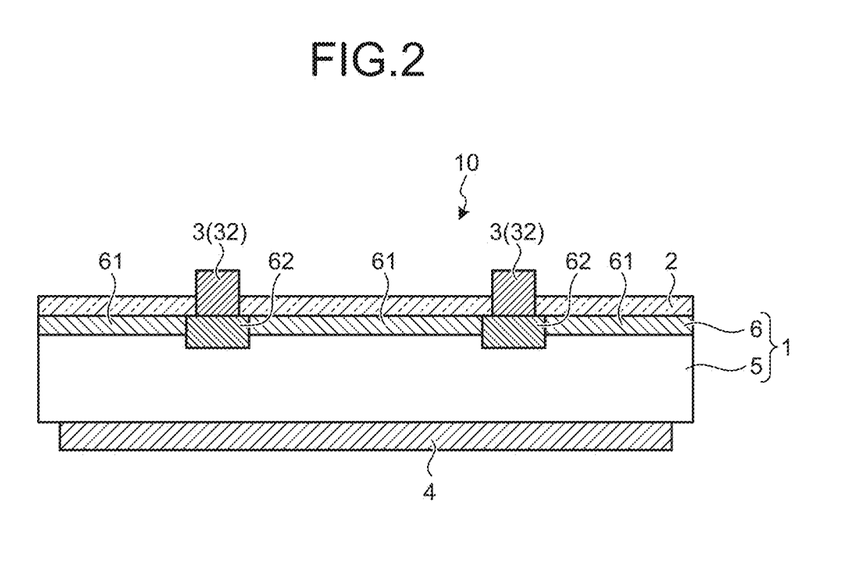
FIG. 2 is a cross-sectional diagram of the solar cell taken along a line II-II in FIG. 1.

FIG. 2 is a cross-sectional diagram of the solar cell 10 taken along a line II-II in FIG. 1. As illustrated in FIG. 2, the solar cell 10 includes the semiconductor substrate 1, the anti-reflective film 2, and the light-receiving-side electrode 3 as described above, and also includes a back-side electrode 4 provided on the back side of the semiconductor substrate 1. The semiconductor substrate 1 includes a main body 5 and a diffusion layer 6 positioned on a light-receiving side of the main body 5. The semiconductor substrate 1 including the main body 5 and the diffusion layer 6 is constituted by, for example, a monocrystalline silicon wafer. The main body 5 has P-type conductivity, for example. The diffusion layer 6 has an opposite conductivity type to that of the main body 5, that is for example, N-type conductivity. The main body 5 and the diffusion layer 6 constitute a P-N junction. The diffusion layer 6 includes a first section 61 having a first concentration of impurities and having a first resistance value, and a second section 62 having a second concentration of the impurities that is higher than the first concentration, and having a second resistance value that is smaller than the first resistance value. The first section 61 is a section that receives light such as solar light. The light-receiving-side electrode 3 is provided on the second section 62. FIG. 2 illustrates the bus electrodes 32 of the light-receiving-side electrode 3.

Figure 3:
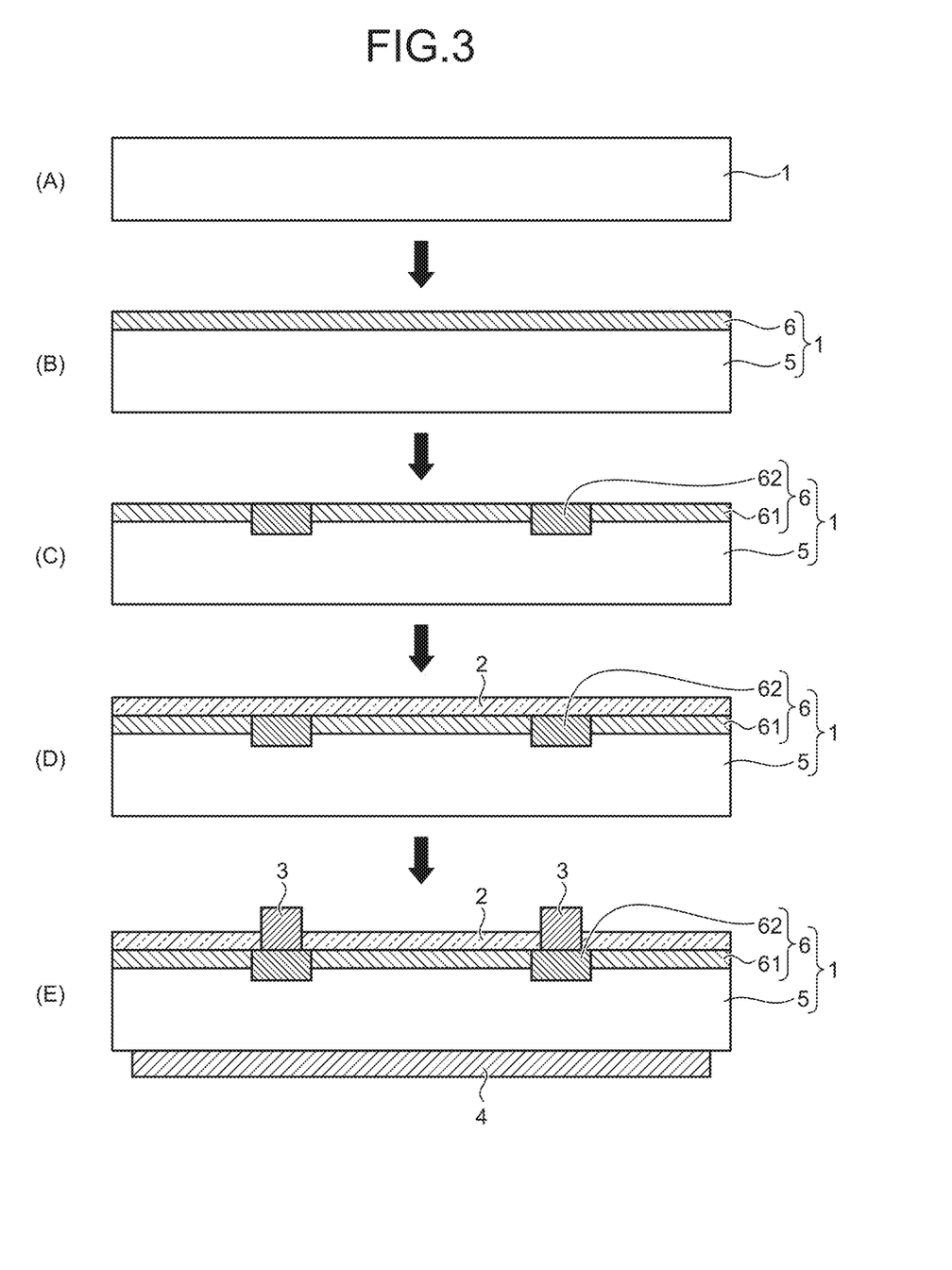
FIG. 3 are diagrams illustrating a procedure of the solar cell manufacturing method according to the first embodiment.

Next, the solar cell manufacturing method according to the first embodiment is described. FIG. 3 are diagrams illustrating a procedure of the solar cell manufacturing method according to the first embodiment. First, a sliced semiconductor substrate 1 is prepared. A slicing damaged layer is removed from the surface of the semiconductor substrate 1 by etching with an alkaline solution or mixed acid. The semiconductor substrate 1 has P-type conductivity, for example. Next, in order to increase the amount of light to be absorbed, a textured structure with fine irregularities is formed on the surface of the semiconductor substrate 1. In order to form the textured structure, an alkaline solution mixed with an additive is added in an etching bath, and then heated to a temperature of approximately 70° C. to 100° C. The semiconductor substrate 1 is soaked in the alkaline solution. In this manner, a pyramid structure on the basis of anisotropy of silicon crystal is formed on the surface of the semiconductor substrate 1, for example. As a result, the textured structure is formed. As illustrated in FIG. 3(A), the semiconductor substrate 1 formed with the textured structure on the surface is prepared. In FIG. 3(A), the textured structure is not illustrated to simplify the illustration of the solar cell manufacturing method.

Next, in order to form a P-N junction in the semiconductor substrate 1, phosphorus atoms are diffused on the surface of a P-type monocrystalline silicon semiconductor substrate 1, which has been heated to approximately 800° C., by a vapor-phase diffusion method in a phosphorus oxychloride (POCl$_3$) gas, for example. An N-type diffusion layer 6 is thereby formed on the surface of the P-type monocrystalline silicon semiconductor substrate 1 as illustrated in FIG. 3(B). A portion of the semiconductor substrate 1, other than the diffusion layer 6, is the main body 5 of the semiconductor substrate 1. At the time of forming the diffusion layer 6, diffusion of phosphorus atoms is limited in such a manner that the resistance value of the diffusion layer 6 becomes, for example, 100Ω/□. On the surface of the diffusion layer 6, a phosphosilicate glassy layer is formed by diffusing phosphorus atoms.

Next, a section of the diffusion layer 6 on the light-receiving side of the semiconductor substrate 1, where the second section 62 is intended to be formed, is irradiated with light from a laser. As described above, the phosphosilicate glassy layer has been formed on the surface of the diffusion layer 6. A section of the phosphosilicate glassy layer, irradiated with light from the laser, is heated by the light. Phosphorus atoms in the heated section are selectively diffused, immediately below the heated section, into a section of the diffusion layer 6, and a section of the main body 5 on the light-receiving side. The section diffused with phosphorus atoms has a higher concentration of phosphorus atoms than the other section where phosphorus atoms are not diffused. The section diffused with phosphorus atoms has a smaller resistance value than the other section where phosphorus atoms are not diffused.

Figure 4:
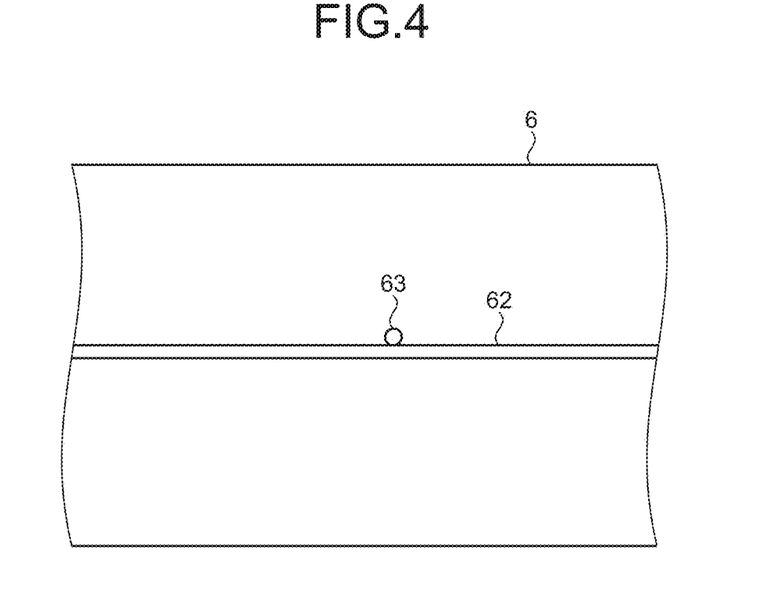
FIG. 4 is a plan view of a part of a diffusion layer for explaining an alignment mark that specifies a position of a second section in the diffusion layer of the solar cell in FIG. 2.

In this manner, the diffusion layer 6 including the first section 61 and the second section 62 is formed on the light-receiving side of the semiconductor substrate 1 as illustrated in FIG. 3(C). The first section 61 has the first concentration of the impurities, and has the first resistance value. The second section 62 has the second concentration of the impurities that is higher than the first concentration, and has the second resistance value that is smaller than the first resistance value. In the first embodiment, the impurities are phosphorus atoms. The second section 62 includes an alignment mark 63 having, for example, a circular shape as illustrated in FIG. 4. FIG. 4 is a plan view of a part of the diffusion layer 6 for explaining the alignment mark 63 that specifies the position of the second section 62 in the diffusion layer 6 of the solar cell 10 in FIG. 2.

Next, the phosphosilicate glassy layer formed on the surface of the diffusion layer 6 is removed by etching. Thereafter, as illustrated in FIG. 3(D), the anti-reflective film 2 is formed on the diffusion layer 6. The anti-reflective film 2 is a silicon nitride film. The silicon nitride film is formed by, for example, plasma-enhanced chemical vapor deposition (PE-CVD). Subsequently, as illustrated in FIG. 3(E), the light-receiving-side electrode 3 is formed on the second section 62 of the diffusion layer 6. The back-side electrode 4 is also formed on the back side of the semiconductor substrate 1. The light-receiving-side electrode 3 is formed by a screen printing technique after the semiconductor substrate 1 formed with the anti-reflective film 2 is placed on a stage of a printing machine. At this time, in order to overlap the light-receiving-side electrode 3 on the second section 62, detection light is used to detect the second section 62 for forming the light-receiving-side electrode 3 thereon.

Figure 5:
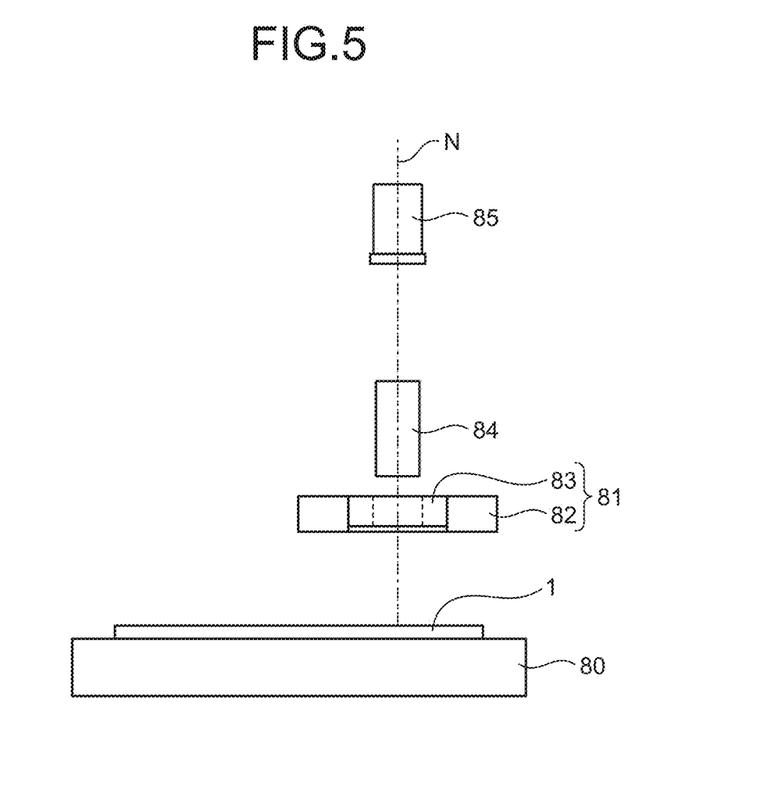
FIG. 5 is a schematic diagram illustrating a plurality of units to detect a section for forming a light-receiving-side electrode thereon by using detection light.

Next, there is described a specific method to detect the second section 62 for forming the light-receiving-side electrode 3 thereon by using detection light. First, a plurality of units which are used to implement the method to detect the second section 62 are described. FIG. 5 is a schematic diagram illustrating a plurality of units to detect a section for forming the light-receiving-side electrode 3 thereon by using detection light. As illustrated in FIG. 5, the semiconductor substrate 1 is placed on a stage 80. A ring-shaped illumination unit 81, a lens 84, and a camera 85 are used to detect a section for forming the light-receiving-side electrode 3 thereon.

The ring-shaped illumination unit 81 includes an infrared-light illumination unit 82 having an annular shape, and a detection-light illumination unit 83 having an annular shape provided on an inner side of the infrared-light illumination unit 82. The infrared-light illumination unit 82 emits infrared light. The detection-light illumination unit 83 is, for example, a light-emitting diode, and emits detection light. The detection light is reflected at a higher reflectivity on the first section 61 than on the second section 62. Furthermore, even when the detection light has passed through the anti-reflective film 2 twice, the detection light is reflected at a higher reflectivity on the first section 61 than on the second section 62.

Figure 6:
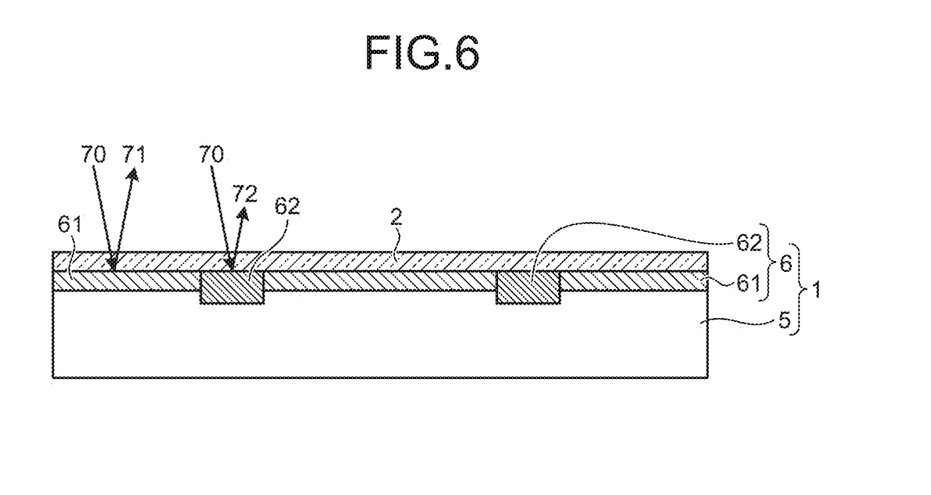
FIG. 6 is a schematic diagram illustrating a fact that when the detection light has passed through an anti-reflective film twice, the detection light is reflected off a first section as reflective light at a higher reflectivity than the detection light that is reflected off the second section as reflective light.

FIG. 6 is a schematic diagram illustrating a fact that when detection light 70 has passed through the anti-reflective film 2 twice, the detection light 70 is reflected off the first section 61 as reflective light 71 at a higher reflectivity than the detection light 70 that is reflected off the second section 62 as reflective light 72. In FIG. 6, an arrow representing the reflective light 71 of the detection light 70 reflected off the first section 61 is longer than an arrow representing the reflective light 72 of the detection light 70 reflected off the second section 62. This schematically indicates that the reflectivity of the reflective light 71 to the detection light 70 on the first section 61 is higher than the reflectivity of the reflective light 72 to the detection light 70 on the second section 62. The detection light 70 has a wavelength between 392 nm and 470 nm. As described above, the detection-light illumination unit 83 has an annular shape, and therefore there is a cavity on the inner side of the detection-light illumination unit 83. As an example of the ring-shaped illumination unit 81, a ring-shaped illuminator named "MITDR-50/28UV-405" and manufactured by IMAC Co., Ltd, can be used.

When the annular detection-light illumination unit 83 irradiates light on the diffusion layer 6 of the semiconductor substrate 1 placed on the stage 80, the lens 84 condenses reflective light from the diffusion layer 6. The lens 84 is located on the normal N relative to the stage 80, on which the semiconductor substrate 1 is placed prior to forming the light-receiving-side electrode 3, that is a line passing through the inner side of the annular detection-light illumination unit 83, at a position further away from the stage 80 than the detection-light illumination unit 83. The camera 85 captures an image formed by the reflective light condensed by the lens 84. The camera 85 is located on the normal N described above at a position further away from the stage 80 than the lens 84.

Figure 7:
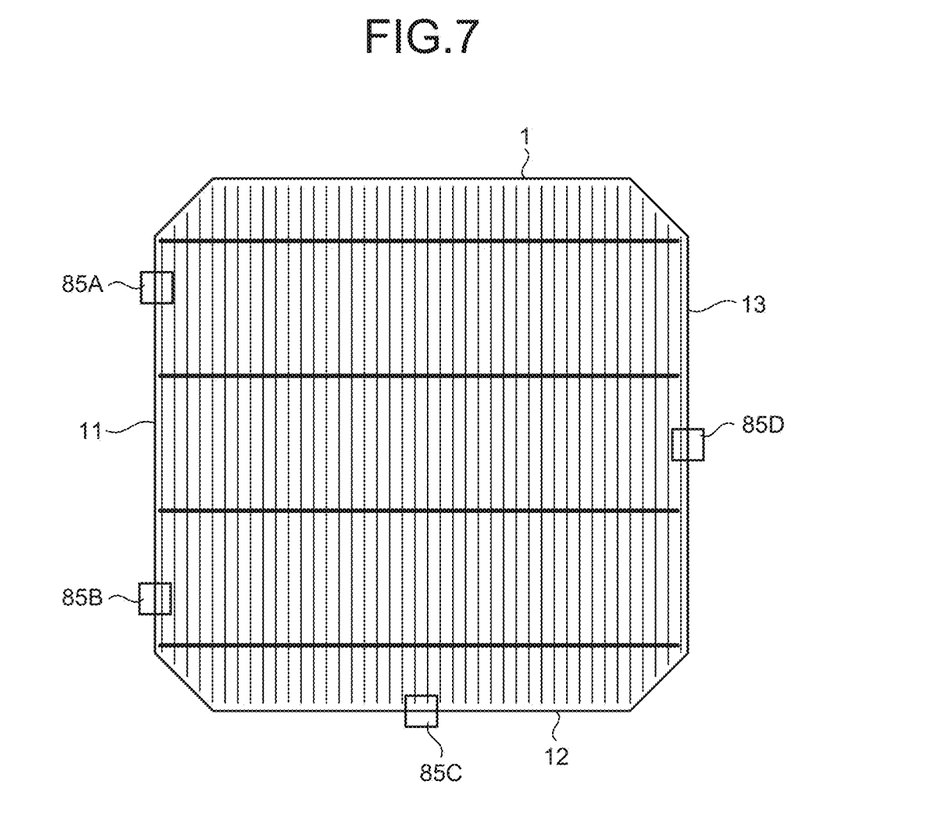
FIG. 7 is a plan view illustrating a light-receiving side of a semiconductor substrate prior to forming the light-receiving-side electrode.

FIG. 7 is a plan view illustrating the light-receiving side of the semiconductor substrate 1 prior to forming the light-receiving-side electrode 3. In FIG. 7, the semiconductor substrate 1 has a planar shape in which four corners of the square are cut diagonally at an angle of 45° relative to the two adjacent sides of each corner. A camera 85A and a camera 85B are provided on a first side 11 of the four sides of the square described above. A camera 85C is provided on a second side 12 thereof. A camera 85D is provided on a third side 13 thereof. The second side 12 is adjacent to the first side 11 and the third side 13. The first side 11 and the third side 13 are opposite to each other. That is, in FIG. 7, the semiconductor substrate 1 is observed from three of the four sides of the above described square by the cameras 85A, 85B, 85C, and 85D.

In a method of detecting the second section 62 of the diffusion layer 6 by using the ring-shaped illumination unit 81 including the detection-light illumination unit 83, the lens 84, and the camera 85, the diffusion layer 6 is irradiated with the detection light 70 that is reflected at a higher reflectivity on the first section 61 of the diffusion layer 6 than on the second section 62. On the basis of a difference in reflectivity of the detection light 70 reflected off the respective sections of the diffusion layer 6, the first section 61 and the second section 62 of the diffusion layer 6 are detected. The first section 61 corresponds to a first reflectivity which is relatively high. The second section 62 corresponds to a second reflectivity which is lower than the first reflectivity.

More specifically, the first section 61 that corresponds to the first reflectivity, and the second section 62 that corresponds to the second reflectivity which is lower than the first reflectivity are detected on the basis of a difference in brightness in each image formed by light that is reflective light of the detection light 70, condensed by the lens 84 and obtained by each of the cameras 85A, 85B, 85C, and 85D. The difference in brightness appears on the basis of the difference in reflectivity of the detection light 70 reflected off the respective sections of the diffusion layer 6.

As described above, even when the detection light 70 has passed through the anti-reflective film 2 twice, the detection light 70 is reflected at a higher reflectivity on the first section 61 than on the second section 62. The detection light 70 passes through the anti-reflective film 2 twice from when the detection light 70 is irradiated from the detection-light illumination unit 83 to when the detection light 70 is incident to the camera 85. Therefore, on the basis of a difference in reflectivity obtained by using the detection light 70, the second section 62 can be detected. As described above with reference to FIG. 4, the second section 62 includes the circular alignment mark 63. Accordingly, in a case of detecting the second section 62, attention is focused particularly on the alignment mark 63, and thereby the second section 62 can be detected more quickly and precisely.

Figure 8:
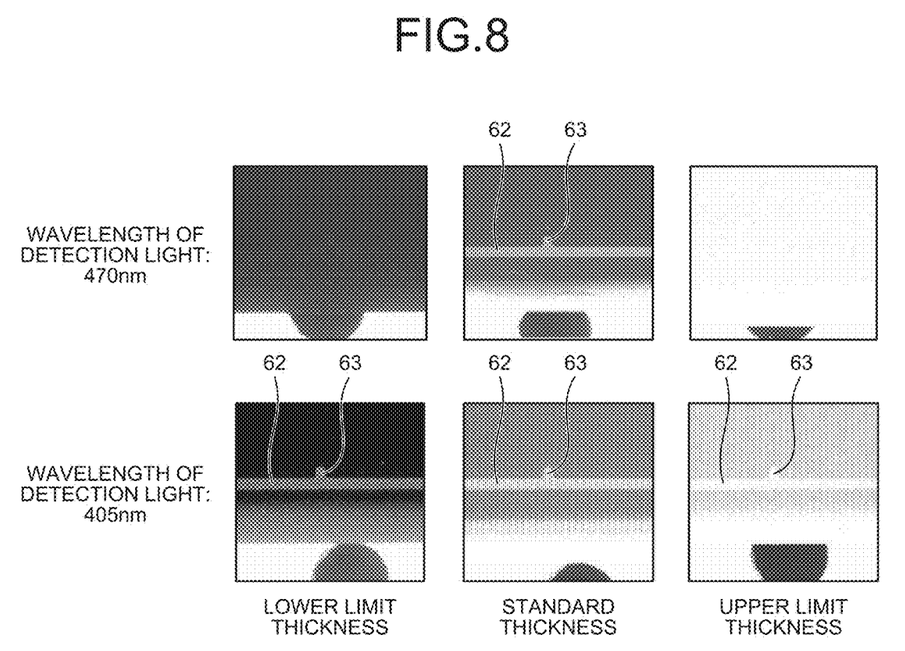
FIG. 8 is a diagram illustrating a correspondence relation between a wavelength of the detection light and an image formed by reflective light.

FIG. 8 is a diagram illustrating a correspondence relation between a wavelength of the detection light 70 and an image formed by reflective light. FIG. 8 illustrates individual images when the anti-reflective film 2 has a lower limit thickness, a standard thickness, and an upper limit thickness, respectively, in both cases where the detection light 70 has a wavelength of 405 nm, and where the detection light 70 has a wavelength of 470 nm. The anti-reflective film 2 has a thickness between the lower limit thickness and the upper limit thickness. The standard thickness is a thickness between the lower limit thickness and the upper limit thickness.

Figure 9:
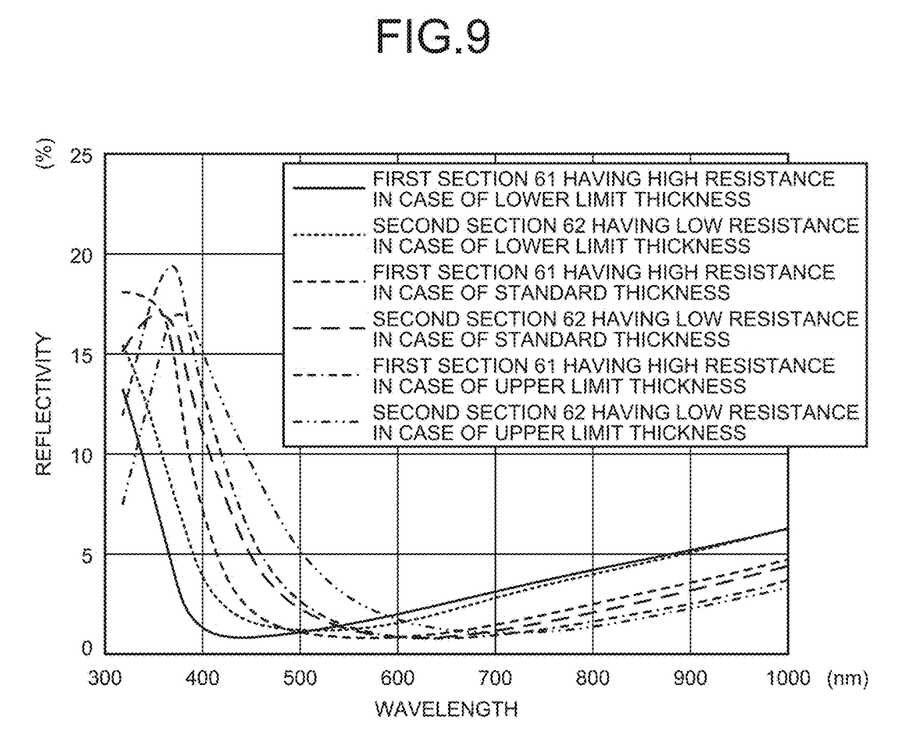
FIG. 9 is a diagram illustrating a relation between a reflectivity and an incident-light wavelength in the first section having a relatively high resistance and in the second section having a relatively low resistance, in respective cases where the anti-reflective film has a lower limit thickness, a standard thickness, and an upper limit thickness.

The first section 61 which occupies 90% or more of the area of the light-receiving surface is important for solar cells to achieve high energy efficiency, and is taken into consideration for its external appearance. The first section 61 has a higher resistance than the second section 62. FIG. 9 is a diagram illustrating a relation between a reflectivity and an incident-light wavelength in the first section 61 having a relatively high resistance and in the second section 62 having a relatively low resistance, in respective cases where the anti-reflective film 2 has the lower limit thickness, the standard thickness, and the upper limit thickness. The reflectivity is represented as a percentage.

As illustrated in FIG. 9, the reflectivity is dependent on the wavelength, while being dependent on the thickness of the anti-reflective film 2. When an anti-reflective film with a refractive index within a range from 2 to 2.2 is used, the thickness of the anti-reflective film is expressed based on relation of wavelength dependence of a reflectance spectrum to a thickness of the anti-reflective film where the wavelength is changed within a range from 30 nm to 120 nm. In this case, the reflectivity relative to the wavelength shows a tendency that the curves generally have a concave section recessed toward the lower reflectivity as illustrated by each curve in FIG. 9. As the anti-reflective film becomes thicker, the wavelength that corresponds to the lowest reflectivity or its vicinity, which is around the lowest portion of the concave section, shifts from a lower wavelength side to a higher wavelength side.

As illustrated in FIG. 9, in a case where the anti-reflective film 2 has the lower limit thickness, the incident-light wavelength is 444 nm at which the reflectivity becomes lowest on the first section 61 with a relatively high resistance. In a case where the anti-reflective film 2 has the standard thickness, the incident-light wavelength is 576 nm at which the reflectivity becomes lowest on the first section 61. In a case where the anti-reflective film 2 has the upper limit thickness, the incident-light wavelength is 638 nm at which the reflectivity becomes lowest on the first section 61.

As illustrated in FIG. 9, in a case where the anti-reflective film 2 has the lower limit thickness, the incident-light wavelength at which the reflectivity becomes lowest on the second section 62 with a relatively low resistance, where an electrode is to be formed later, is 503 nm. In a case where the anti-reflective film 2 has the standard thickness, the incident-light wavelength at which the reflectivity becomes lowest on the second section 62 is 617 nm. In a case where the anti-reflective film 2 has the upper limit thickness, the incident-light wavelength at which the reflectivity becomes lowest on the second section 62 is 732 nm.

That is, the lower limit thickness described above is a thickness when the incident-light wavelength is 444 nm at which the reflectivity becomes lowest on the first section 61, and when the incident-light wavelength is 503 nm at which the reflectivity becomes lowest on the second section 62. The standard thickness described above is a thickness when the incident-light wavelength is 576 nm at which the reflectivity becomes lowest on the first section 61, and when the incident-light wavelength is 617 nm at which the reflectivity becomes lowest on the second section 62. The upper limit thickness described above is a thickness when the incident-light wavelength is 638 nm at which the reflectivity becomes lowest on the first section 61, and when the incident-light wavelength is 732 nm at which the reflectivity becomes lowest on the second section 62.

As described above, each of the lower limit thickness, the standard thickness, and the upper limit thickness of the anti-reflective film 2 is indicated by the incident-light wavelength at which the reflectivity becomes lowest respectively on the first section 61 with a relatively high resistance and on the second section 62 with a relatively low resistance. A textured structure with fine irregularities is formed on the surface of the semiconductor substrate 1. Therefore, it is very difficult to directly evaluate the thickness of the anti-reflective film 2 whose film thickness is in a nanometer order by using a measurement unit of length. In addition, in terms of actual management of the film thickness, the dependency of reflectivity on wavelength is commonly used. Accordingly, in the present application, the lower limit thickness, the standard thickness, and the upper limit thickness of the anti-reflective film 2 are individually defined by the incident-light wavelength at which the reflectivity becomes lowest respectively on the first section 61 with a relatively high resistance and on the second section 62 with a relatively low resistance.

As is apparent when focusing attention particularly on the alignment mark 63 in FIG. 8 in relation to the lower limit thickness, the standard thickness, and the upper limit thickness of the anti-reflective film 2, which have been described with reference to FIG. 9, when the detection light 70 has a wavelength of 405 nm, a difference in brightness appears in each image regardless of whether the anti-reflective film 2 has either the lower limit thickness, the standard thickness, or the upper limit thickness. Due to this difference, the first section 61 and the second section 62 of the diffusion layer 6 can be accurately detected. The first section 61 corresponds to the first reflectivity which is relatively high. The second section 62 corresponds to the second reflectivity which is lower than the first reflectivity. In the individual images in FIG. 8, a section where the reflectivity is lower is shown in lighter colors, while a section where the reflectivity is higher is shown in darker colors by image processing.

In a case where the detection light 70 has a wavelength of 470 nm, the brightness of the image is substantially uniform when the anti-reflective film 2 has the lower limit thickness and when the anti-reflective film 2 has the upper limit thickness. Therefore, it is difficult to detect the first section 61 and the second section 62. The anti-reflective film 2 of an actual product has a thickness between the above lower limit thickness and upper limit thickness. Taking into account the results in FIG. 8, it is desirable that the detection light 70 has a wavelength of 405 nm in order to detect the second section 62 for forming the light-receiving-side electrode 3 thereon. However, as is apparent from FIG. 8, in a case where the anti-reflective film 2 has the standard thickness, even when the detection light 70 with a wavelength of 470 nm is used, the first section 61 and the second section 62 can still be accurately detected.

Figure 10:
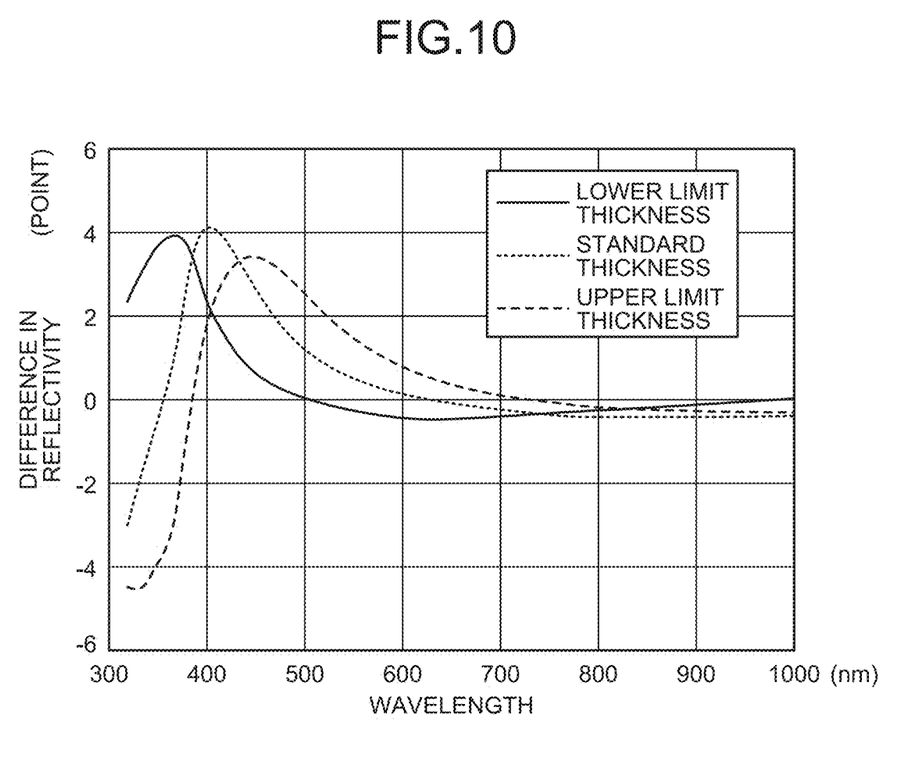
FIG. 10 is a diagram illustrating a relation between a light wavelength and a difference in reflectivity between the first section having the relatively high resistance and the second section having the relatively low resistance in respective cases where the anti-reflective film has the lower limit thickness, the standard thickness, and the upper limit thickness.

FIG. 10 is a diagram obtained on the basis of FIG. 9. FIG. 10 is a diagram illustrating a relation between a light wavelength and a difference in reflectivity between the first section 61 and the second section 62 in respective cases where the anti-reflective film 2 has the lower limit thickness, the standard thickness, and the upper limit thickness. In the first section 61, the impurity concentration is relatively low, and the resistance value is relatively high. In the second section 62, the impurity concentration is relatively high, and the resistance value is relatively low. As illustrated in FIG. 10, a peak of the difference in reflectivity between the first section 61 and the second section 62 appears at a shorter light wavelength as the anti-reflective film 2 becomes thinner.

Figure 11:
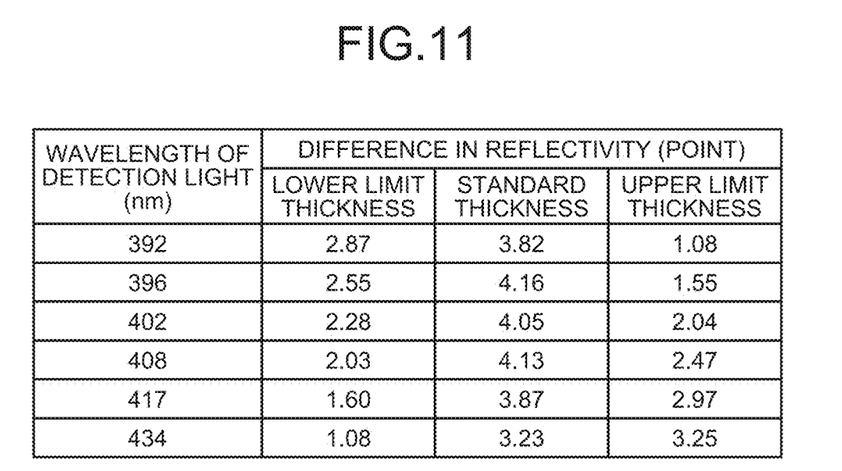
FIG. 11 is a diagram illustrating a difference in reflectivity between the first section having the relatively high resistance and the second section having the relatively low resistance, relative to six different wavelengths of the detection light in respective cases where the anti-reflective film has the lower limit thickness, the standard thickness, and the upper limit thickness.

FIG. 11 is a diagram obtained on the basis of FIG. 10 and the like. FIG. 11 is a diagram illustrating a difference in reflectivity between the first section 61 and the second section 62 relative to six different wavelengths of the detection light 70 in respective cases where the anti-reflective film 2 has the lower limit thickness, the standard thickness, and the upper limit thickness. In the first section 61, the impurity concentration is relatively low, and the resistance value is relatively high. In the second section 62, the impurity concentration is relatively high, and the resistance value is relatively low. The six different wavelengths are 392 nm, 396 nm, 402 nm, 408 nm, 417 nm, and 434 nm. A difference in reflectivity between the first section 61 and the second section 62 is represented by points on the basis of the absolute value of the difference in reflectivity between the first section 61 and the second section 62 relative to each of the wavelengths.

As is apparent from FIG. 11, where the detection light 70 has a wavelength equal to or longer than 396 nm and equal to or shorter than 417 nm, the difference in reflectivity between the first section 61 and the second section 62 can become equal to or greater than 1.5 points regardless of whether the anti-reflective film 2 has either the lower limit thickness, the standard thickness, or the upper limit thickness. Consequently, the first section 61 and the second section 62 can be accurately detected. When the detection light 70 has a wavelength equal to or longer than 402 nm and equal to or shorter than 408 nm, the difference in reflectivity between the first section 61 and the second section 62 can become equal to or greater than 2 points regardless of whether the anti-reflective film 2 has either the lower limit thickness, the standard thickness, or the upper limit thickness. Consequently, the first section 61 and the second section 62 can be more accurately detected.

As described above, in the solar cell manufacturing method according to the first embodiment, the diffusion layer 6 including the first section 61 and the second section 62 is formed on the light-receiving side of the semiconductor substrate 1. The first section 61 has the first concentration of the impurities and has the first resistance value. The second section 62 has the second concentration of the impurities that is higher than the first concentration and has the second resistance value that is smaller than the first resistance value. Thereafter, the diffusion layer 6 is irradiated with the detection light 70 that is reflected at a higher reflectivity on the first section 61 than on the second section 62, and that has a wavelength between 392 nm and 470 nm. On the basis of a difference in reflectivity of the detection light 70 reflected off the respective sections of the diffusion layer 6, the first section 61 that corresponds to the first reflectivity, and the second section 62 that corresponds to the second reflectivity which is lower than the first reflectivity in the diffusion layer 6 are detected. Subsequently, the light-receiving-side electrode 3 is formed on the detected second section 62.

In the conventional method that uses three points on an outer periphery of a semiconductor substrate as reference points to detect the position where a light-receiving-side electrode should be formed, the installation position of the semiconductor substrate may become slightly misaligned. Therefore, it is very difficult to accurately detect the position where the light-receiving-side electrode should be formed. Thus, a method has been conventionally used in which by increasing the area of a high impurity-concentration section of a diffusion layer relative to the size of a light-receiving-side electrode, and the light-receiving-side electrode is still formed on the high impurity-concentration section even when the position of the light-receiving-side electrode is misaligned to some degree.

However, according to the above method, the high impurity-concentration section is partially positioned in a low impurity-concentration region of the diffusion layer, which is originally a light-receiving region. Consequently, the high impurity-concentration section receives light. Many of electrons and positive holes that are photocarriers created by light incident to the high impurity-concentration section are recombined on the light-receiving side of the semiconductor substrate, and thereby dissipate. Therefore, the efficiency of conversion from optical energy to power is decreased. In the conventional method that uses three points on an outer periphery of a semiconductor substrate as reference points to detect the position where a light-receiving-side electrode should be formed, it is also conceivable that the size of the light-receiving-side electrode is made larger than the area of the high impurity-concentration section. In that case, however, the light-receiving area is decreased which causes a problem that the efficiency of conversion from optical energy to power is decreased.

Because the solar cell manufacturing method according to the first embodiment does not use transmissive light, the manufacturing method according to the first embodiment does not require a device having a complicated configuration. Further, the manufacturing method according to the first embodiment does not require special materials such as silicon nanoparticles.

As described above, in the manufacturing method according to the first embodiment, on the basis of a difference in reflectivity of the detection light 70 reflected off respective sections of the diffusion layer 6, the first section 61 that corresponds to the first reflectivity, and the second section 62 that corresponds to the second reflectivity which is lower than the first reflectivity in the diffusion layer 6 are detected. That is, in the manufacturing method according to the first embodiment, instead of indirectly detecting the position where the light-receiving-side electrode 3 should be formed with respect to an outer periphery of the semiconductor substrate, the position where the light-receiving-side electrode 3 should be formed is directly detected on the basis of a difference in reflectivity of the detection light 70.

Therefore, the manufacturing method according to the first embodiment can prevent detection errors, which cannot be avoided by the conventional method that uses three points on an outer periphery of a semiconductor substrate as reference points to detect the position where the light-receiving-side electrode 3 should be formed. The manufacturing method according to the first embodiment can accurately detect the position where the light-receiving-side electrode 3 should be formed. Accordingly, the manufacturing method according to the first embodiment can form the light-receiving-side electrode 3 accurately at an intended position. That is, the solar cell manufacturing method according to the first embodiment can accurately detect the position where the light-receiving-side electrode 3 should be formed, and form the light-receiving-side electrode 3 at the detected position without a device having a complicated configuration and without requiring special materials. As a result, a solar cell manufactured by the solar cell manufacturing method according to the first embodiment can convert optical energy to power with high efficiency.

In the first embodiment, the solar cell 10 includes the anti-reflective film 2. However, it is permissible that the solar cell 10 does not include the anti-reflective film 2. Even in that case, because the detection light 70 is reflected at a higher reflectivity on the first section 61 than on the second section 62, it is obvious that the position where an electrode should be formed can be accurately detected on the basis of a difference in reflectivity of the detection light 70.

As described above with reference to FIG. 11, when the detection light 70 has a wavelength equal to or longer than 396 nm and equal to or shorter than 417 nm, the difference in reflectivity between the first section 61 and the second section 62 can become equal to or greater than 1.5 points regardless of whether the anti-reflective film 2 has either the lower limit thickness, the standard thickness, or the upper limit thickness. Consequently, the first section 61 and the second section 62 can be accurately detected. When the detection light 70 has a wavelength equal to or longer than 402 nm and equal to or shorter than 408 nm, the difference in reflectivity between the first section 61 and the second section 62 can become equal to or greater than 2 points regardless of whether the anti-reflective film 2 has either the lower limit thickness, the standard thickness, or the upper limit thickness. Consequently, the first section 61 and the second section 62 can be more accurately detected.

As is apparent from FIG. 8, in a case where the anti-reflective film 2 has the standard thickness, even when the detection light 70 has a wavelength of 470 nm, the first section 61 and the second section 62 can still be accurately detected. In addition, as is apparent from FIG. 11, in a case the anti-reflective film 2 has the lower limit thickness or the standard thickness, even when the detection light 70 has a wavelength of 392 nm, the difference in reflectivity between the first section 61 and the second section 62 can become equal to or greater than 2.5 points. Consequently, the first section 61 and the second section 62 can be accurately detected.

Therefore, as understood from FIG. 8 and FIG. 11, it suffices that the detection light 70 has a wavelength equal to or longer than 392 nm and equal to or shorter than 470 nm in a case where the anti-reflective film 2 has the standard thickness. It also suffices that the detection light 70 has a wavelength equal to or longer than 392 nm and equal to or shorter than 417 nm in a case where the anti-reflective film 2 has the lower limit thickness. It also suffices that the detection light 70 has a wavelength equal to or longer than 396 nm and equal to or shorter than 434 nm in a case where the anti-reflective film 2 has the upper limit thickness. In either case where the anti-reflective film 2 has the lower limit thickness, the standard thickness, or the upper limit thickness, it is preferable that the detection light 70 has a wavelength equal to longer than 396 nm and equal to shorter than 417 nm in order to accurately detect the first section 61 and the second section 62. It is more preferable that the detection light 70 has a wavelength equal to longer than 402 nm and equal to shorter than 408 nm.

In the first embodiment, the ring-shaped illumination unit 81 including the detection-light illumination unit 83, the lens 84, and the camera 85 are used as illustrated in FIG. 5 to detect the second section 62 for forming the light-receiving-side electrode 3 thereon. By using the lens 84 and the camera 85, an image can be formed in which a difference in reflectivity between the first section 61 and the second section 62 can be visually recognized. Consequently, the first section 61 and the second section 62 can be accurately detected.

The detection light 70 is not limited to light emitted from the annular detection-light illumination unit 83. The detection-light illumination unit 83 is not limited to a light-emitting diode. It is sufficient that the detection light 70 is reflected at a higher reflectivity on the first section 61 than on the second section 62. Furthermore, it is sufficient that the detection light 70 is reflected at a higher reflectivity on the first section 61 than on the second section 62, even when the detection light 70 has passed through the anti-reflective film 2 twice. In addition, it is sufficient that the detection light 70 has a wavelength between 392 nm and 470 nm. When an illumination unit can irradiate the detection light 70 as described above, it is possible that this illumination unit is used in place of the annular detection-light illumination unit 83.

As described above, by using the lens 84 and the camera 85, an image can be formed in which a difference in reflectivity between the first section 61 and the second section 62 can be visually recognized. However, it is also possible that units other than the lens 84 and the camera 85 are used to detect the second section 62 for forming the light-receiving-side electrode 3 thereon. For example, the second section 62 can also be detected by using a unit that measures the reflectivity on the first section 61 and the reflectivity on the second section 62, and that displays a difference in the measured reflectivity between the first section 61 and the second section 62 on a two-dimensional plane. In either case, on the basis of a difference in reflectivity of the detection light 70 reflected off the respective sections of the diffusion layer 6, the first section 61 that corresponds to the first reflectivity, and the second section 62 that corresponds to the second reflectivity which is lower than the first reflectivity in the diffusion layer 6 are detected. The first section 61 and the second section 62 can thereby be detected accurately.

In the first embodiment, the first section 61 and the second section 62 are formed in the diffusion layer 6 by laser doping using laser light. The first section 61 has a relatively low concentration of the impurities and has the first resistance value. The second section 62 has a relatively high concentration of the impurities and has the second resistance value that is smaller than the first resistance value. However, the method to form the first section 61 and the second section 62 in the diffusion layer 6 is not limited to laser doping. For example, it is possible that the first section 61 and the second section 62 are formed in the diffusion layer 6 by a printing technique and a drying process by applying dopant paste containing phosphorus atoms on the light-receiving side of the diffusion layer 6, and then heating the dopant paste in a diffusion furnace.

In the above method using dopant paste, the dopant paste is heated in a diffusion furnace to a temperature from 870° C. to 940° C. to diffuse phosphorus atoms only into a section where the dopant paste has been applied. Thereafter, the temperature in the diffusion furnace is decreased to approximately 800° C. to diffuse phosphorus chloride into a section where the dopant paste has not been applied. Subsequently, the phosphosilicate glassy layer is etched.

In the method using dopant paste, the resistance value of the first section 61 with the relatively low concentration of the impurities can be set to 90Ω/□ to 100Ω/□. Also, the concentration of phosphorus atoms that are impurities in the first section 61 can be set to $5 \times 10^{20}$ to $2 \times 10^{21}$ (atoms/cm$^3$). In the second section 62 with the relatively high concentration of the impurities, the resistance value can be set to 20Ω/□ to 80Ω/□. Also, the concentration of phosphorus atoms that are impurities in the second section 62 can be set to $5 \times 10^{19}$ to $2 \times 10^{20}$ (atoms/cm$^3$). As an example of the above dopant paste, a product named "YT-2100-N" and manufactured by Hitachi Chemical Co., Ltd. can be used.

In the embodiment described above, the laser doping method or the method using dopant paste is used as a method to form the first section 61 and the second section 62 in the diffusion layer 6. However, as a method to form the first section 61 and the second section 62 in the diffusion layer 6, it is possible that any selective-emitter formation method is used such as a commonly-known ion implantation method or etch-back method.

In the embodiment described above, prior to forming the diffusion layer 6, the semiconductor substrate 1 has, for example, P-type conductivity. It is also possible that prior to forming the diffusion layer 6, the semiconductor substrate 1 has N-type conductivity. In a case where the semiconductor substrate 1 has N-type conductivity prior to forming the diffusion layer 6, when the solar cell manufacturing method according to the first embodiment is used, it is possible to manufacture a solar cell with a selective back surface field or a selective front surface field.

The configurations described in the above embodiment are only examples of the content of the present invention. The configurations can be combined with other well-known techniques, and a part of the configuration can be omitted or modified without departing from the scope of the present invention.

REFERENCE SIGNS LIST 10 solar cell, 1 semiconductor substrate, 2 anti-reflective film, 3 light-receiving-side electrode, 31 grid electrode, 32 bus electrode, 4 back-side electrode, 5 main body, 6 diffusion layer, 61 first section, 62 second section, 63 alignment mark, 70 detection light, 80 stage, 81 ring-shaped illumination unit, 82 infrared-light illumination unit, 83 detection-light illumination unit, 84 lens, 85 camera.

The invention claimed is:

1. A solar cell manufacturing method comprising:
   a step of forming a diffusion layer including a first section and a second section on a light-receiving side of a semiconductor substrate, where the first section has a first concentration of impurities and has a first resistance value, and the second section has a second concentration of the impurities that is higher than the first concentration and has a second resistance value that is smaller than the first resistance value;
   a step of forming an anti-reflective film that is a silicon nitride film on the diffusion layer, where the step of forming the anti-reflective film is performed after the step of forming the diffusion layer,
   a step of irradiating the diffusion layer with detection light that is reflected at a higher reflectivity on the first section than on the second section, and that has a wavelength between 392 nm and 470 nm, the detection light passing through the anti-reflective film, where the step of irradiating the diffusion layer is performed after the step of forming the anti-reflective film;
   a step of detecting the first section that corresponds to a first reflectivity, and the second section that corresponds to a second reflectivity that is lower than the first reflectivity in the diffusion layer on a basis of a difference in reflectivity of the detection light reflected off respective sections of the diffusion layer; and
   a step of forming a light-receiving-side electrode on the detected second section,
   wherein the second section includes a linear section and an alignment mark contacting the linear section, and
   wherein, at the step of detecting the first section and the second section, the second section is detected by focusing on the alignment mark.

2. The solar cell manufacturing method according to claim 1, wherein even when the detection light has passed through the anti-reflective film twice, the detection light is reflected at a higher reflectivity on the first section than on the second section.

3. The solar cell manufacturing method according to claim 2, wherein
   the anti-reflective film has a thickness between a lower limit thickness and an upper limit thickness,
   the lower limit thickness is a thickness when an incident-light wavelength is 444 nm at which a reflectivity becomes lowest on the first section, and when an incident-light wavelength is 503 nm at which a reflectivity becomes lowest on the second section,
   a standard thickness between the lower limit thickness and the upper limit thickness is a thickness when an incident-light wavelength is 576 nm at which a reflectivity becomes lowest on the first section, and when an incident-light wavelength is 617 nm at which a reflectivity becomes lowest on the second section,
   the upper limit thickness is a thickness when an incident-light wavelength is 638 nm at which a reflectivity becomes lowest on the first section, and when an incident-light wavelength is 732 nm at which a reflectivity becomes lowest on the second section, and
   regardless of whether the anti-reflective film has either the lower limit thickness, the standard thickness, or the upper limit thickness, the detection light is reflected at a higher reflectivity on the first section than on the second section when the detection light has passed through the anti-reflective film twice.

4. The solar cell manufacturing method according to claim 1, wherein a wavelength of the detection light is between 402 nm to 408 nm.

5. The solar cell manufacturing method according to claim 1, wherein
   the detection light is emitted from an annular detection-light illumination unit, and
   at the step of detecting the first section and the second section, a lens and a camera are used to detect the second section on a basis of a difference in brightness of an optical image obtained by the camera, that is a difference that appears on a basis of a difference in reflectivity of the detection light reflected off respective sections of the diffusion layer, where the lens is located on a normal relative to a stage, on which the semiconductor substrate is arranged, that is a line passing through an inner side of the detection-light illumination unit, at a position further away from the stage than the detection-light illumination unit, and where the camera is located on the normal at a position further away from the stage than the lens.

* * * * *